(12) United States Patent
Pews

(10) Patent No.: US 7,462,728 B2
(45) Date of Patent: Dec. 9, 2008

(54) **DIEPOXIDE DERIVATIVES OF N,N*-DISUBSTITUTED DISULFONAMIDES**

(76) Inventor: R. Garth Pews, 4830 Osprey Dr., South, Apt. 603, St Petersburg, FL (US) 33711

( * ) Notice: Subject to any disclaimer, the term of this patent is extended or adjusted under 35 U.S.C. 154(b) by 653 days.

(21) Appl. No.: 11/012,829

(22) Filed: Dec. 15, 2004

(65) Prior Publication Data

US 2006/0128978 A1 Jun. 15, 2006

(51) Int. Cl.
*C07D 303/36* (2006.01)
(52) U.S. Cl. .................................... 549/552
(58) Field of Classification Search ................ 549/548, 549/552
See application file for complete search history.

(56) References Cited

U.S. PATENT DOCUMENTS 3,945,973 A * 3/1976 Smith et al. ................ 528/210

2004/0099840 A1 * 5/2004 Horsham et al. ....... 252/188.28

* cited by examiner

*Primary Examiner*—Bernard Dentz
(74) *Attorney, Agent, or Firm*—Bernd W. Sandt

(57) ABSTRACT

The present invention relates to novel diepoxides having the formulas I. and II.

$$R^*N(A)SO_2RSO_2N(A)R^* \qquad \text{I}$$

$$R^*SO_2N(A)RN(A)SO_2R^* \qquad \text{II}$$

where A=2,3-epoxypropyl, R* is a monovalent hydrocarbon alkyl aryl, aryl-alkyl, alkyl-aryl radical of 1-20 carbon atoms or a monovalent inertly substituted hydrocarbon aryl, alkyl, alkyl-aryl or aryl-alkyl radical of 1-20 carbons atoms and R is a divalent hydrocarbon arylene, alkylene, alkylene-aryl, arylene-alkyl radical or combinations thereof of 2-20 carbon atoms or an inertly substituted divalent hydrocarbon alkylene, arylene, arylene-alkyl, or alkylene-aryl radical or combinations thereof of 2-20 carbon atoms. The epoxides are useful in preparing novel epoxide resins.

3 Claims, No Drawings

DIEPOXIDE DERIVATIVES OF N,N*-DISUBSTITUTED DISULFONAMIDES

BACKGROUND OF THE INVENTION

The epoxy intermediates and resins industry (Encyclopedia of Chemical Technology, Volume 9, Fourth Edition, John Wiley & Sons Page 370) is a multimillion dollar business that is based on the following technology that involves no less than eleven chemical reactions.

benzene+propylene→isopropylbenzene
isopropylbenzene→cumene hydroperoxide
cumene hydroperoxide→phenol+acetone
phenol+acetone→bisphenol A (bisA)
propylene+chlorine→allyl chloride+hydrochloric acid (HCl)
allyl chloride+sodium hydroxide+chlorine→propylene chlorohydrins
propylene chlorohydrins+sodium hydroxide→epichlorohydrin
bisA+epichlorohydrin→bisA chlorohydrin
bisA chlorohydrin+sodium hydroxide→bisA diepoxide
bisA diepoxide+bisA→epoxy resin
sodium chloride+water->chlorine+sodium hydroxide
waste chlorinated byproducts+hydrogen→HCl+hydrocarbons Several aspects of the above reaction sequence have negative process implications with regard to yields, chlorinated byproducts, hydraulic load and biological hazards. These include but are not limited to the following: (a) benzene is a known carcinogen, (b) BisA is an endocrine disrupter (mimics estrogen). Recent research (Current Biology, Volume 13, page 546, 2003) has shown that abnormalities in developing mouse eggs would lead to miscarriages and birth defects, (c) chlorination of propylene to allyl chloride and the addition of hypochlorous acid to allyl chloride yield higher chlorinated products resulting ~⅓ pounds of chlorinated waste per pound of epichlorohydrin. In addition, the process requires a chloralkali facility, hence a local supply source of salt and huge volumes of water. The products and processes of the present invention ameliorate if not eliminate some of the disadvantages of prior art of epoxy products and processes.

BRIEF DESCRIPTION OF THE INVENTION

The present invention relates to novel diepoxide derivatives of disulfonamides for use as intermediates (comonomer) in the preparation of epoxy resins. The diepoxides of the invention are represented by the following formulas I. and II.

   I

   II where A is 2,3-epoxypropyl, R* is a monovalent hydrocarbon alkyl aryl, aryl-alkyl, alkyl-aryl radical of 1-20 carbon atoms or a monovalent inertly substituted hydrocarbon aryl, alkyl, alkyl-aryl or aryl-alkyl radical of 1-20 carbons atoms and R is a divalent hydrocarbon arylene, alkylene, alkylene-aryl, arylene-alkyl radical or combinations thereof of 2-20 carbon atoms or an inertly substituted divalent hydrocarbon alkylene, arylene, arylene-alkyl, or alkylene-aryl radical or combinations thereof of 2-20 carbon atoms. The term "inertly substituted" is defined as substituents on the hydrocarbon radicals that do not interfere in the reaction scheme employed to prepare the novel epoxides of the present invention. Such substituents would be apparent to those skilled in the art from the reactions set forth and are primarily halogen, ether, ester and amide substituents. Preferred mono and divalent aromatic moieties are derived from hydrocarbons which include but are not limited to benzene, naphthalene, toluene, chlorobenzene, xylene, biphenyl, phenyl ether, phenyl sulfone and benzophenone. Preferred aryl alkyl moieties are derived from hydrocarbons, which include benzyl, bibenzyl, 1,2-diphenoxyethane, and 1,4-diphenoxybutane. Preferred alkyl moieties include but are not limited to ethyl, propyl, hexyl, octyl, cyclohexyl and methoxyethyl.

DETAILED DESCIPTION OF THE INVENTION

The preferred synthetic route to the desired disulfonamide diepoxides requires the synthesis of N,N*-substituted disulfonamides, as the precursor of the desired diepoxides. There are two synthetic routes to the N,N*-disubstituted disulfonamides, the reaction of two equivalents of a primary amine with a disulfonyl dichloride (equation 1) and the reaction of two equivalents of sulfonyl dichloride with one equivalent of a primary diamine (equation 2).

$$R(SO_2Cl)_2 + 2R^*NH_2 \rightarrow R^*NHSO_2RSO_2NHR^* \quad \text{equation 1}$$

$$2R^*SO_2Cl + NH_2RNH_2 \rightarrow R^*SO_2NHRNHSO_2R^* \quad \text{equation 2}$$

where R and R* have the indicated meanings.

The preparation of diaromatic disulfonyl chlorides is well documented in the literature and is achieved via the sulfonation or chlorosulfonation of aromatic compounds ("Friedel-Crafts and Related Reactions", Volume 3. Part 2, page 1355, Interscience Publishers, 1964; C. M. Suter, "Organic Chemistry of Sulfur Compounds", Chapter 3, John Wiley and Sons, 1944; "Organic Functional Group Preparations", S. Sandler and W. Karo, Academic Press 1968, page 506). The reactions are preferably carried out in 1,2-dichloromethane as a solvent. If higher reaction temperatures are required for the bis sulfonation, the reaction may be performed without a solvent. Aliphatic sulfonyl chlorides are prepared via chlorination of the sulfuric acids with chlorosufonic acid. Methanesulfonyl chloride is readily available via radical chlorination of methane in the presence of sulfur dioxide. (R. Wagner and H. Zook, Synthetic Organic Chemistry, page 821, J. Wiley & Sons 1953). The synthesis of amines has been reviewed. (M. B. Smith in Compendium of Organic Synthetic Methods, Vol. 8, page 139, John Wiley & Sons, New York 1995). The conversion of N,N*-disubstituted disulfonamides may be transformed to the desired diepoxides via the utilization of either epichlorohydrin or the allyl acetate as illustrated:

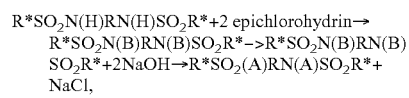

where A=2,3-epoxypropyl and B=2-hydroxy-3-chloropropyl.

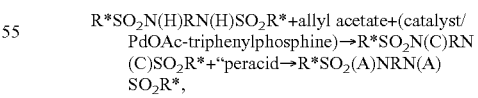

where A is 2,3-epoxypropyl and C is allyl.

Development of the allyl acetate technology has significant potential advantages over the present "epichlorohydrin-Bisphenol-A technology" for the manufacture of epoxy resins. These advantages are as follows: (a) significant reduction of chlorinated wastes, (b) elimination of a capital intensive chlor-alkali facility, (c) unlike the loss of chlorine and caustic to brine in the present process, the initial sulfur dioxide from sulfonation is incorporated into the diepoxide molecule. As demonstrated, the peracid oxidation of an allyl sulfonamide is feasible, whereas the oxidation of ally phenyl ethers of the BisA process is very slow and yields are lower due to oxidation of the aromatic rings and resulting purification problems.

The condensation of the diepoxides of this invention with diphenols, e.g., Bisphenol-A, Bisphenol-F, 4-hydroxyphenyl sulfone, 4,4*-dihydroxybenzophenone, 4,4*-dihydroxybiphenyl, and 1,4-(4-hydoxyphenyl)butane, with dicarboxylic acids, e.g., isophthalic acid, succinic acid, and cyclohexane dicarboxylic acids, with amino phenols, e.g., 4-aminophenol, 4-amino-4*-hydroxyphenyl ether, and 4-amino-4*-hydroxybiphenyl, with hydroxycarboxylic acids, e.g., 4-hydroxybenzoic acid, and 6-hydroxy-2-naphthoic acid, with amino acids, e.g., 4-aminobenzoic acid, with diamines, e.g., 4,4*-diaminophenyl ether, 1,3-diaminobenzene and 1,3-diaminopropane or with disulfonamides, e.g. 1,3-benzenedisulfonic acid: bis N methylamide results in a new and valuable epoxy resins for protective coatings, structural composites, laminates and adhesives. The condensation is carried out using methods developed for established epoxy resins and is extensively described in the literature and patents.

The chemistry used in the diepoxides of the present invention provides the opportunity to manufacture resins with fewer chemical transformations, less capital and a reduction in the waste load associated with the bisA/epichlorohydrin technology. The resins can be obtained from diepoxides using condensation procedures known in the art. An example of a resin from readily available starting materials using a diepoxide route of the present invention is outlined below:

1. $SO_2 \rightarrow SO_3 \rightarrow ClSO_3H$
2. benzene $\rightarrow$ 1,3-benzenesulfonyl chloride
3. 1,3-benzenesulfonyl chloride+$2CH_3NH_2 \rightarrow$ N,N*-dimethyl-1,3-benzenedisulfonamide
4. propylene $\rightarrow$ allyl acetate
5. & 6. N,N*-dimethyl-1,3-benzenedisulfonamide $\rightarrow$ N,N*-dimethyl-N,N*-diallyl-1,3-benzenedisulfonamide $\rightarrow$ N,N*-dimethyl-N,N*-bis(2,3-epoxypropyl)-1,3-benzenedisulfonamide.
7. N,N*-dimethyl-1,3-benzenedisulfonamide+N,N*-dimethyl-N,N*-bis(2,3-epoxypropyl)-1,3-benzenedisulfonamide $\rightarrow$ epoxy resin The following examples further illustrate novel epoxides of the present invention but are not intended to be limiting.

EXAMPLE 1

Preparation of N,N*-Bis(2,3-Epoxypropy)-N,N*-Bis (Cyclohexyl)-2,5-Dimethyl-1,3-Benzenedisulfonamide Cyclohexylamine (4.49 g, 0.045 mol) and triethylamine (8.5 ml) were diluted with tetrahydrofuran (100 ml) and added to a tetrahydrofuran (25 ml) solution of 2,5-dimethyl-1,3-benzenesulfonyl dichloride. After the addition was complete, the reaction mixture was refluxed for 2 hrs, cooled and poured onto ice water. The precipitate that was formed, N,N*-cyclohexyl-2,5-dimethyl-1,3-benzenedisulfonamide, was filtered and dried, mp 201-203° C. MS m/z 428 (M+ calcd for $C_{20}H_{22}N_2O_4S_2$=428). H NMR (300 Mhz, dmso-d6), d 0.98-1.22 (m, 5, $CH_2$), 1.43-1.54 (m, 8, $CH_2$), 2.41 (s, 3, $CH_3$), 2.60 (s, 3, $CH_3$), 2.88 (m, 2, CH), 7.82 (t, 2, NH), 7.97 (s, 2, aromatic).

N,N*-cyclohexyl-2,5-dimethyl-1,3-benzenedisulfonamide (3.21 g, 0.0075 mol) was dissolved in 2-propanol (100 ml). 50% Sodium hydroxide (1.20 g) and tetraethyl ammonium chloride (0.05 g) were added to the solution and the solution refluxed for 1 hr. Epichlorohydrin (5 g) was added and the solution refluxed for 12.5 hrs and cooled to room temperature. The solvent, 2-propanol was removed in vacuo and the residue dissolved in dichloromethane and washed (2×) with water, dried over anhydrous $MgSO_4$ and evaporated in vacuo. The crude bischlorohydrin was diluted with dichloromethane (50 ml) and added to a 50% sodium hydroxide (2.5 g) and tetraethyl ammonium chloride (50 mg) and the reaction mixture stirred for 2 hrs at room temperature. The organic layer was washed with water (2×), dried over anhydrous potassium carbonate and evaporated to give N,N*bis(2,3-epoxypropyl)-N,N*-bis(cyclohexyl)-2,5-dimethyl-1,3-benzenedisulfonamide. Recrystallization from hexane-ethyl acetate gave product mp 110-115° C. MS m/z 540 (M+ calcd for $C_{26}H_{40}N_2O_6S_2$=540). H NMR (300 MHz, $CDCl_3$) d 1.05-1.91 (m, 20, $CH_3$), 2.45 (s, 3, $CH_3$ aromatic), 2.52 (m, 2, epoxypropyl $CH_2$), 2.77 (s, 3, $CH_3$ aromatic), 2.81 (m, 2, $CH_2$ epoxypropyl), 3.08 (m, 2, CH cyclohexyl), 3.14 (m, 2, CH, epoxypropyl), 3.57 (m, 4, $CH_2$ epoxypropyl), 8.08 (s, 2, aromatic).

EXAMPLE 2

Preparation of N,N*-Bis-2,3-Epoxypropyl-N,N*-Bis (N-Butyl)-4,4-Phenyl Ether Disulfonamide 4,4*-Phenyl ether disulfonyl dichloride (8.85 g, 0.023 mol) was dissolved in tetrahydrofuran (100 ml) and a mixture of n-butyl amine (3.66 gm, 0.05 mol) and triethylamine (7 ml) were added to the sulfonyl chloride solution at room temperature. After the addition was complete, the reaction mixture was refluxed for one hour, cooled and poured onto ice-water. The product was extracted with dichloromethane (200 ml) and the dichloromethane solution dried over anhydrous $MgSO_4$. Evaporation of the dichloromethane and recrystallization from methanol gave N,N*-bis(n-butyl)-4,4*-phenyl ether disulfonamide mp 137-140° C. MS m/z 440. (Calcd for $C_{20}H_{28}N_2O_5S_2$=440). H NMR (300 MHz, dmso-d6) d 0.82 (6, t, $CH_3$), 1.18-1.40 (m, 8, $CH_2$), 2.76 (m, 4, $NCH_2$), 7.28 (m, 4, aromatic), 7.56 (m, 2, NH), 7.85 (m, 4, aromatic).

N,N*-bis(n-butyl)-4,4*-phenyl ether disulfonamide(3.0 gm, 0.007 mol) was refluxed overnight in epichlorohydrin (10 ml). After cooling, the excess epichlorohydrin was removed in vacuo and product diluted with dichloromethane (50 ml). 50% Sodium hydroxide (3.0 gm) and tetraethyl ammonium hydroxide (100 mg) was added to the solution and the solution stirred for two hours at room temperature. The dichloromethane solution was washed with water (2×), dried over anhydrous potassium carbonate. Evaporation of the solvent in vacuo and recrystallization from acetone-hexane gave N,N*-bis(2,3-epoxypropyl)-N,N*-bis(n-butyl)-4,4*-phenyl ether disulfonamide, mp 113-115° C. MS m/z 552. (M+ calcd for $C_{26}H_{40}N_2O_7S_2$=552). H NMR (300 Mhz, $CDCl_3$) d 0.92 (t, 3, $CH_3$), 1.32 (m, 2, $CH_2$), 2.55 (m, 1, $CH_2$, epoxypropyl), 2.80 (m, 1, $CH_2$ epoxypropyl), 2.97 (q, 1, $CH_2$ epoxypropyl), 3.08 (m, 1, CH epoxypropyl), 3.12-3.34 (m, 2, $NCH_2$), 3.64 (q, 1, $CH_2$ epoxypropyl), 7.13 (m, 2, aromatic), 7.84 (m, 2, aromatic).

EXAMPLE 3

Preparation of N,N*-Bis(2,3-Epoxypropyl)-N,N*-Bis(2-Methoxyethyl)-4,4 *Biphenyldisulfonamide Methoxyethylamine (3.0 g, 0.04 mol) and triethylamine (7 ml) were diluted with tetrahydrofuran (20 ml) and added drop wise to solution of 4,4*-biphenyl sulfonyl dichloride(7.04 gm, 0.02 mol) in tetrahydrofuran (80 ml). After the addition was complete, the reaction was refluxed for 1 hr, cooled and poured onto ice-water. The precipitate was filtered, and dried to give N,N*-methoxyethyl-4,4*-biphenyl disulfonamide mp 148-150° C. MS m/z 428 (M+ calcd for $C_{18}H_{12}N_2O_6S_2$=428. H NMR (300 Mhz, dmso-d6) d 2.92 (m, 4, $CH_2$), 3.15 (s, 6, $OCH_3$), 3.32 (m, 4, $CH_2N$), 7.82-8.01 (m, 8, aromatic), 8.11 (m, 2, NH).

N,N*-methoxyethyl-4,4*-biphenyl disulfonamide (3.212 g, 0.0075 mol) was dissolved in epichlorohydrin and refluxed overnight. After cooling, excess epichlorohydrin was removed in vacuo and the residue dissolved in dichloromethane (50 ml) and added to 50% sodium hydroxide (2.5 g) and tetraethyl ammonium chloride (100 mg). The reaction mixture was stirred for 2 hrs. The dichloromethane solution was washed with water (2×) and dried over potassium carbonate. Evaporation of the solvent and recrystallization of the product gave N,N*-bis(2,3-epoxypropyl)-N,N*-bis2-methoxymethyl)-4,4*-biphenyldisulfonamide mp 102-105° C. MS m/z 495. (M+ minus $C_2H_{30}$) (M+ calcd for $C_{24}H_{32}N_2O_8S_2$=540). H NMR (300 Mhz, $CDCl_3$) d 2.55 (m, 2, $CH_2$ epoxypropyl), 2.80 (m, 2, $CH_2$), 2.99 (s, 3, $CH_3$), 3.20 (m, 2, CH epoxypropyl), 3.68 (m, 2, $CH_2$ epoxypropyl), 3.90 (m, 2, $CH_2$ epoxypropyl), 7.05 (m, 4, aromatic), 7.36 (m, 4, aromatic).

EXAMPLE 4

Preparation of N,N*-Bis(2,3-Epoxypropyl)-N,N*Bis (Phenyl)-2,6-Napthalene Disulfonamide 2,6-Naphthalene disulfonyl chloride (2.3 g, 0.007 mol) was dissolved in chloroform (25 ml) and added dropwise to a chloroform (50 ml) solution of triethylamine (2 ml) and aniline (1.34 g, 0.014 mol) at room temperature. After the addition was complete, the reaction mixture was refluxed for 1 hr. After cooling, the organic solution was washed with water (2×), dried over anhydrous magnesium sulfate and the solvent evaporated in vacuo. The product, N,N*-bis(phenyl)-2,6-naphthalene disulfonamide, after recrystallization from dichloromethane-hexane had mp 178-180° C. MS m/z 438. (M+ calcd for $C_{22}H_{18}N_2S_2O_4$=438). H NMR 300 MHz dmso-d6) d 6.97-7.25 (m, 10, phenyl), 7.86 (d, 2, naphthalene), 8.49 (d, 2, naphthalene), 10.48 (s, 2, NH).

N,N*-bis(phenyl)-2,6-naphthalene disulfonamide (1.01 g) was refluxed in epichlorohydrin (10 ml) overnight. After cooling, the excess epichlorohydrin was evaporated in vacuo. The bis chlorohydrin was diluted with dichloromethane (60 ml, not completely soluble). 50% Sodium hydroxide (2.0 gm) and tetraethyl ammonium chloride were added to the dichloromethane solution and the solution stirred for 2.5 hr at room temperature. The insoluble starting material dissolved during the epoxidation. The dichloromethane solution was washed with water (2×). After solvent evaporation in vacuo and recrystallization from ethyl acetate-hexane, N,N*-bis (2,3-epoxypropyl)-N,N*-(phenyl)-2,6-naphthalene had mp 220-222° C. MS m/z 550. (M+ calcd for $C_{28}H_{26}N_2O_6S_2$=550). H NMR (300 Mhz, $CDCl_3$) d 2.47 (m, 1, $CH_2$ epoxypropyl), 2.73 (m, 1, $CH_2$ epoxypropyl), 3.17 (m, 1, CH epoxypropyl), 3.79 (m, 2, $CH_2$ epoxypropyl), 7.10 (m, 3, phenyl), 7.26-7.34 (m, 7, phenyl), 7.70 (d, 2, naphthalene), 7.97 (d, 2, naphthalene), 8.25 (s, 2, naphthalene).

EXAMPLE 5

Preparation of N,N*-Bis(2,3-Epoxypropyl-N,N*-Bis (4-Methylphenylsulfonyl) Ethylene Diamine Ethylene diamine (3.0 g, 0.05 mol) was diluted with toluene (20 ml) and added to a toluene solution of 4-methylphenyl sulfonyl chloride (19.06 g, 0.1 mol) and triethylamine (15 ml). The reaction mixture was refluxed for 2 hrs, cooled and the precipitated triethylamine hydrochloride filtered and the toluene removed in vacuo. The residue, after recrystallization from aqueous methanol gave N,N*-4-bis(methylphenylsulfonyl) ethylene diamine mp 159-162° C. MS m/z 368 (M+ calcd for $C_{16}H_{20}N_2O_4S_2$=368). H NMR (300 Mhz, dmso-d6) d 2.39 (s, 6, $CH_3$), 2.72 (m, 4, $CH_2$), 7.36 (d, 4, aromatic) 7.62 (d, 4, aromatic), 7.60 (s, 2, NH).

N,N*-4-bis(methylphenylsulfonyl) ethylene diamine (3.68 gm, 0.01 mol) was dissolved in epichlorohydrin and refluxed overnight. After cooling, the excess epichlorohydrin was evaporated in vacuo and the crystalline bis chlorohydrin (mp 170-172° C.) was diluted with dichloromethane (50 ml). Tetraethyl ammonium chloride (0.1 gm), and 50% sodium hydroxide (3.0 gm) was added to the dichloromethane solution and the reaction stirred at room temperature for 2 hr. The organic layer was washed with (2×) water, dried over anhydrous potassium carbonate, evaporated and recrystallized from dichloromethane-hexane to give N,N*-bis(2,3-epoxypropyl)-N,N*-bis(-4-methylphenylsulfonyl)ethylene diamine, mp 168-170° C. MS m/z 480 (M+ calcd for $C_{22}H_{28}N_2O_6S_2$=480). H NMR (300 Mhz, $CDCl_3$) d 2.23 (m, 2, $CH_2$ epoxypropyl), 3.47 (m, 2, $CH_2$N), 3.41-3.53 (m, 1, $CH_2$ epoxypropyl), 3.63 (m, 2, $CH_2$ epoxypropyl), 7.32 (2, d, aromatic), 7.77 (2, d, aromatic).

EXAMPLE 6

Preparation of N,N*-Bis(2,3-Epoxypropyl)-N,N*-Bis(4-Methylsulfonyl)-4,4*-Diaminophenyl Ether 4,4*-Diaminophenyl ether (20 g, 0.01 mol) and triethylamine (30 ml) were dissolved in tetrahydrofuran (250 ml) and the solution cooled to 0-5° C. in an ice bath. Methanesulfonyl chloride (22.8 g, 0.2 mol) was added dropwise over 30 min. After the addition was complete, the reaction was stirred for 1 hr and poured onto ice. The product, N,N*-bis (methylsulfonyl)-4,4*-diaminophenyl ether was filtered and dried mp 232-235 C. MS m/z 356 (M+ calcd for $C_{14}H_{16}N_2O_5S_2$=356). H NMR (300 Mhz, dmso-d6) d 2.95 (s, 6, $CH_3$), 6.99 (m, 4, aromatic), 7.21 (m, 4, aromatic), 9.60(s, 2, NH).

N,N*-bis(methylsulfonyl)-4,4*-diaminophenyl ether (3.56 g, 0.01 mol) was diluted with 1,2-dichloromethane and epichlorohydrin (3 g) was added to the solution. The reaction mixture was refluxed for 2 days. The solvent and excess epichlorohydrin was removed in vacuo. The crude bischlorohydrin was diluted with dichloromethane (50 ml) and tetraethyl ammonium chloride (100 mg), 50% sodium hydroxide (3.0 g) were added and the reaction mixture stirred for 2 hrs. The dichloromethane solution was washed with water (2×), dried over anhydrous potassium carbonate and the solvent evaporated to give, after recrystallization from hexane-1,2-dichloromethane, N,N*bis(2,3-epoxypropyl)-N,N*-bis(4-methylsulfonyl)-4,4*-diaminophenyl ether mp 145-148° C. MS m/z 468. (M+ calcd for $C_{20}H_{24}N_2O_7S_2$=468). H NMR (300 Mhz, $CDCl_3$) d 2.55 (m, 1, $CH_2$, epoxypropyl), 2.80 (m, 1, $CH_2$ epoxypropyl), 2.99 (s, 3, $CH_3$), 3.19 (m, 1, CH epoxypropyl), 3.69 (m, 1, $CH_2$ epoxypropyl), 3.90 (m, 1, $CH_2$ epoxypropyl), 7.06 (m, 4, aromatic), 7.38 (m, 4, aromatic).

EXAMPLE 7

Preparation of N,N*-Bis(2,3-Epoxypropyl)-N,N*-Bis(Methanesulfonyl-1,8-Diaminooctane 1,8-Diaminoethane (7.22 g, 0.05 mol) and triethylamine (20 ml) were diluted with tetrahydrofuran (100 ml) and cooled in ice-water. Methanesulfonyl chloride (11.4 g, 0.01 mol) was added dropwise at ~10-15° C. After the addition was complete, the reaction mixture was poured onto ice water to precipitate the product. Filtration and drying gave N,N*-bis(methanesulfonyl)-1,8-diaminooctane mp 135-137° C. MS m/z 300. (M+ calcd for $C_{10}H_{24}N_2O_4S_2$=300). H NMR (300 Mhz, dmso-d6) d 1.27 (s, 8, $CH_2$), 1.45 (m, 4, $CH_2$), 2.88 (s, 6, $CH_3$), 2.92 (m, 4, $CH_2$N), 6.91 (t, 2, NH).

N,N*-bis(methanesulfonyl)-1,8-diaminooctane (3.0 g, 0.01 mol) was dissolved in 2-propanol (100 ml). Tetraethyl ammonium chloride and 50% sodium hydroxide (1.60 g) were added to the reaction mixture and the solution refluxed for 1 hr. Epichlorohydrin (5 g) was added and the reaction mixture refluxed overnight, cooled and the solvent removed in vacuo. The residue was diluted with dichloromethane and the organic phase washed with water (2×) and dried over anhydrous potassium carbonate. Evaporation of the solvent in vacuo gave N,N*-bis(2,3-epoxypropyl)-N,N*-bis(methanesulfonyl)-1,8-diaminooctane as a viscous oil. MS m/z 369 (M+ minus $C_2H_3O$). (M+ calcd for $C_{16}H_{32}N_2O_6S_2$=412). H NMR (300 Mhz, $CDCl_3$) d 1.33 (s, 8, $CH_2$), 1.64 (m, 4, $CH_2$), 2.59 (m, 2, epoxypropyl $CH_2$), 2.83 (m, 2, $CH_2$ epoxypropyl $CH_2$), 2.90 (s, 6, $CH_3$), 3.05 (m, 2, $CH_2$epoxypropyl $CH_2$), 3.16 (m, 2, epoxypropyl CH), 3.28 (m, 4, $CH_2N$), 3.67(m, 2, $CH_2$ epoxypropyl).

EXAMPLE 8

Preparation of N,N*-Bis(2,3-Epoxypropyl)-N,N*-Bis(4-Methylphenyl Sulfonyl-1,3-Phenylenediamine 1,3-Phenylene diamine (4.5 g, 0.025 mol) and pyridine (3.95 g, 0.05 mol) were dissolved in chloroform (80 ml). 4-Methylbenzene sulfonyl chloride (9.5 g, 0.05 mol) was dissolved in chloroform and added dropwise to the amine solution at room temperature. After the addition was complete, the reaction mixture was refluxed for 2 hrs. After cooling, the chloroform was evaporated in vacuo. The residue was dissolved in ethyl acetate and washed with water (2×), dried over anhydrous magnesium sulfate and evaporated to give N,N*-bis(4-methylbenzenesulfonyl)-1,3-phenylenediamine, mp 160-165° C. MS m/z 416. (M+ calcd for $C_{20}H_{20}N_2O_4S_2$=416). H NMR (300 Mhz, dmso-d6). d 2.35 (s, 6, CH3), 6.66 (q, 2, phenylene), 7.01 (t, 1, phenylene), 7.12 (t, 1, phenylene), 7.31 (d, 4, phenyl), 7.59 (d, 4, phenyl).

N,N*-bis(4methylbenzenesulfonyl)-1,3-phenylene diamine (3.0 g, 0.007 mol), and epichlorohydrin(10 ml) were refluxed overnight. After cooling and evaporation of the excess epichlorohydrin in vacuo, the bischlorohydrin was diluted with dichloromethane (50 ml). Tetraethylammonium chloride (100 mg) and 50% sodium hydroxide (2.5 g) were added to the reaction mixture and the solution stirred for 2 hrs at room temperature. The dichloromethane solution was washed with water (2×) dried over anhydrous potassium carbonate. The dichloromethane was evaporated in vacuo and the product recrystallized from ethyl acetate to give N,N*-bis (2,3-epoxypropyl)-N,N*-bis(4-methylbenzenesulfonyl)-1, 3-phenylenediamine, mp 93-95° C. MS m/z 528. (M+ calcd for $C_{26}H_{28}N_2O_6S_2$=528). H NMR (300 Mhz, $CDCl_3$) d 2.42 (s, 6, $CH_2$), 2.44 (m, 1, $CH_2$ epoxypropyl), 3.06 (m, 1, CH, epoxypropyl), 3.63 (d, 2, CH epoxypropyl), 6.86 (m, 1, phenylene), 7.08 (m, 2, phenylene), 7.27 (s, 1, phenylene), 7.43 (m, 4, phenylene), 7.26 (m, 4, phenyl).

EXAMPLE 9

Preparation of N-Methyl-N*-(2,3-Epoxypropyl)-4-Methylbenzenesulfonamide (Method A)

N-methyl-4-methylbenzene sulfonamide (4.0 g) were refluxed for 48 hrs in epichlorohydrin (15 ml). After cooling, the excess epichlorohydrin was removed in vacuo, diluted with dichloromethane (50 ml). Tetraethyl ammonium chloride (50 mg) and 50% sodium hydroxide (3 g) were added to the dichloromethane solution and stirred at room temperature for 2 hr. The reaction mixture was washed with water (2×), dried over anhydrous potassium carbonate and the solvent removed in vacuo to give N-Methyl-N*-2,3-epoxypropyl-4-methylbenezenesulfonamide. MS m/z 241. (M+ calcd for $C_{11}H_{15}NO_2S$=241). H NMR (300 Mhz, CDCl3) d 2.43 (s, 3, $CH_3$), 2.53 (m, 1, $CH_2$ epoxypropyl), 2.76-2.83 (m, 2, $CH_2$ epoxypropyl), 2.84 (s, 3, $NCH_2$), 3.10 (m, 1, CH epoxypropyl), 3.48 (m, 1, $CH_2$ epoxypropyl), 7.44 (m, 2, aromatic), 7.66 (m, 2, aromatic).

EXAMPLE 10

Preparation of N-Methyl-N*-(2,3-Epoxypropyl)-4-Methylbenzenesulfonamide (Method B)

N-methyl-4-methylbenzenesulfonamide (5.55 g, 0.05 mol) was dissolved in 2-propanol (75 ml). Tetraethyl ammonium chloride (0.1 g) and 50% sodium hydroxide (2.40 gm) were added to the solution. Allyl bromide (2.30 g, 0.03 mol) was added to the reaction mixture and the solution stirred for 1 hr. The solution was filtered to remove sodium bromide and the 2-propanol evaporated in vacuo. The crude product was diluted with ethyl acetate and washed with water (2×), dried over anhydrous magnesium sulfate and evaporated in vacuo to give N-methyl-N* allyl-4-methylbenzenesulfonamide. MS m/z 225. (M+ calcd for $C_{11}H_{15}NO_2S$=225). H NMR (300 Mhz, $CDCl_3$) d 2.44 (s, 3, $CH_3$), 2.67 (s, 3, $NCH_3$), 3.63 (m, 2, $CH_2$ epoxypropyl), 5.21 (m, 2, $CH_2$ epoxypropyl), 5.66-5.77 (m, 1, CH epoxypropyl), 7.33 (m, 2, aromatic), 7.67 (m, 2, aromatic).

N-methyl-N*-allyl-4-benzenesulfonamide was also prepared by stirring N-methyl-4-benzenesulfonamide (4.65 g, 0.025 mol), triphenylphosphine (0.1 g), allyl acetate (10 ml) and palladium acetate (50 mg) for 48 hrs. The reaction mixture was diluted with ethyl acetate and the organic solution washed with water (2×), dilute sodium bicarbonate and dried over anhydrous magnesium sulfate. Evaporation in vacuo gave material that was 95% product and <5% starting material. The oxidation of N-methyl-N*allyl-4-methlbenzenesulfonamide with m-chlorobenzene perbenzoic acid in dichloromethane solution overnight gave N-methyl-N*-(2,3-epoxypropyl)-4-methylbenzenesulfonamide. The IR and NMR spectra were identical to product prepared by method A. A similar experiment with peracetic acid at room temperature required longer reaction times (~4-5 days).

What is claimed is:

1. The diepoxide N,N*-bis(2,3-epoxypropyl)-N,N*-bis (cyclohexyl)-2,5-dimethyl-1,3-benzenedisulfonamide having a molecular weight of 540 and a melting point of 110-150° C.

2. The diepoxide N,N*-bis(2,3-epoxypropyl)-N,N*-bis(2-methoxyethyl)-4,4*-biphenyl disulfonamide having a molecular weight of 495 and a melting point of 102-105° C.

3. The diepoxide N,N*-bis(2,3-epoxypropyl)-N,N*-bis (phenyl)-2,6-naphthalene disulfonamide having a molecular weight of 550 and a melting point of 220-220° C.

* * * * *